US009925340B2

(12) United States Patent
Glocker

(10) Patent No.: US 9,925,340 B2
(45) Date of Patent: Mar. 27, 2018

(54) SYRINGE CLOSURE

(71) Applicant: Vetter Pharma-Fertigung GmbH & Co. KG, Ravensburg (DE)

(72) Inventor: Joachim Glocker, Weingarten (DE)

(73) Assignee: Vetter Pharma-Fertigung GmbH & Co. KG, Ravensburg (DE)

( * ) Notice: Subject to any disclaimer, the term of this patent is extended or adjusted under 35 U.S.C. 154(b) by 0 days.

(21) Appl. No.: 14/707,553

(22) Filed: May 8, 2015

(65) Prior Publication Data
US 2015/0238703 A1    Aug. 27, 2015

Related U.S. Application Data

(63) Continuation of application No. PCT/EP2013/073320, filed on Nov. 8, 2013.

(30) Foreign Application Priority Data

Nov. 9, 2012    (DE) ........................ 10 2012 022 008

(51) Int. Cl.
*A61M 5/32* (2006.01)
*A61M 5/34* (2006.01)
(Continued)

(52) U.S. Cl.
CPC ........ *A61M 5/3202* (2013.01); *A61M 5/3204* (2013.01); *A61M 5/344* (2013.01);
(Continued)

(58) Field of Classification Search
CPC ........ A61M 2005/3104; A61M 5/5086; A61M 39/20; A61M 5/344; A61M 2005/3106;
(Continued)

(56) References Cited

U.S. PATENT DOCUMENTS 5,554,134 A * 9/1996 Bonnichsen ............ A61M 5/24
604/232
6,196,998 B1 * 3/2001 Jansen ................ A61M 5/3134
604/111
(Continued)

FOREIGN PATENT DOCUMENTS

DE    102011015112    9/2012
EP    1647294    4/2006
(Continued)

OTHER PUBLICATIONS

International Search Report of corresponding International Application No. PCT/EP2013/073320, dated Jan. 1, 2014.
(Continued)

*Primary Examiner* — Bhisma Mehta
*Assistant Examiner* — Brandy S Lee
(74) *Attorney, Agent, or Firm* — Edell, Shapiro & Finnan, LLC

(57) ABSTRACT

The invention relates to a syringe closure for a syringe having a basic body, a terminal extension that extends from the basic body, which has a free end and a base arranged on the basic body. A recess is provided on the extension at a distance from its free end. The syringe closure for closing off the syringe can be attached in such a way on its extension via its free end that the syringe closure overlaps at least one recess of the extension. The syringe closure is characterized by a locking device having at least one locking element, which assumes a release position in a first functional position after the attachment of the syringe closure on the extension, and ensures a positive engagement with at least one recess on the extension in a second functional position, the locking position, and thus lockingly holds the syringe closure on the extension.

11 Claims, 1 Drawing Sheet

(51) Int. Cl.
  *A61M 5/50* (2006.01)
  *A61M 5/31* (2006.01)
(52) U.S. Cl.
  CPC .......... *A61M 5/345* (2013.01); *A61M 5/347* (2013.01); *A61M 5/5086* (2013.01); *A61M 2005/312* (2013.01); *A61M 2005/3104* (2013.01); *A61M 2005/3106* (2013.01)
(58) Field of Classification Search
  CPC .......... A61M 39/1011; A61M 5/3202; A61M 5/3204; A61M 5/345; A61M 5/347; A61M 5/50; A61M 2005/312
  See application file for complete search history.

(56) References Cited

U.S. PATENT DOCUMENTS

2004/0087906 A1* 5/2004 Henderson .......... A61M 5/3134
   604/187
2012/0031904 A1 2/2012 Kuhn et al.

FOREIGN PATENT DOCUMENTS

| EP | 1693079 | 8/2006 |
|---|---|---|
| WO | 2004052432 | 6/2004 |
| WO | 2006087763 | 8/2006 |
| WO | 2011124632 | 10/2011 |
| WO | 2012116792 | 9/2012 |

OTHER PUBLICATIONS

English language International Preliminary Report on Patentability and Written Opinion for International Patent Application No. PCT/EP2013/073320, dated May 12, 2015.

* cited by examiner

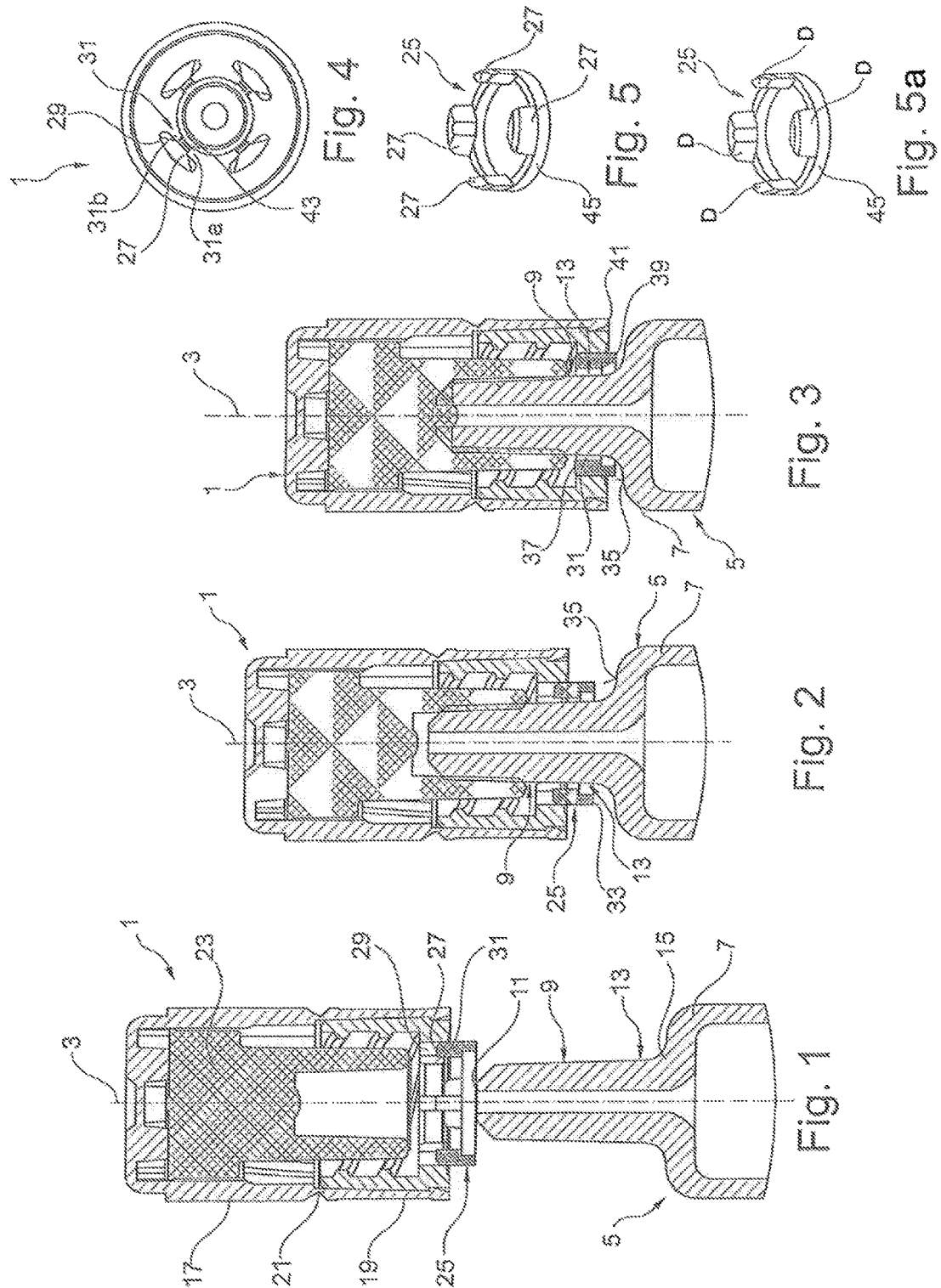

SYRINGE CLOSURE

CROSS REFERENCE TO RELATED APPLICATIONS

This application is a continuation of International Application No. PCT/EP2013/073320, filed on Nov. 8, 2013, which claims priority under 35 U.S.C. § 119 to Application No. DE 102012022008.1 filed on Nov. 9, 2012, the entire contents of which are hereby incorporated by reference.

FIELD OF THE INVENTION

The invention relates to a syringe closure for a syringe.

BACKGROUND

Syringe closures of the kind addressed herein are generally known. They are usually configured as a tamper evident safety seal, namely in such a way that unauthorized manipulation of the closure can be readily detected by a user. The injection closure is pressed onto a terminal extension, which, as a rule, has a conical configuration and extends from the basic body of the syringe. At least one recess, which preferably has an annular configuration, is provided on the extension at a distance from its free end. After attaching the syringe closure, said syringe closure snaps into the recess with its rim located in the area of the recess and is held in this way on the extension. In order to ensure a secure closure of the syringe it should not be possible to pull the syringe closure off the extension. A relative rotation between the syringe and the closure should also be prevented. Therefore, it is necessary to generate a strong clamping force. In order to ensure this, it is provided that the syringe closure abuts securely in the area of the recess wherein the outer diameter is smaller in the area of the recess than in the directly adjacent area of the extension. In the known syringe closures, it is provided that they are expanded when they are attached on the extension, so that they find a secure hold on the extension by snapping back into the recess.

It has been determined that relatively high pressure forces are required during the attachment of the syringe closure on the extension, which could cause a break in the syringe usually made of glass. It has also been shown that overextending the material of the syringe closure during the attachment can show signs of fatigue, which prevents a secure hold of the syringe closure on the syringe.

SUMMARY

It is therefore the object of the invention to create a syringe closure that provides a secure hold on a syringe, and does not have the mentioned disadvantages.

The syringe closure is characterized by a locking device with at least one locking element, which assumes a release position in a first functional position after the syringe closure is attached on the extension of a syringe. The term "release position" herein expresses that the syringe closure is seated more or less loosely on the extension and at best very low retaining forces are generated which are not sufficient to ensure the required secure hold of the syringe closure on the syringe, especially on its extension. Different from the known systems, the syringe is expanded very little during a first attachment of the syringe closure on a syringe and is only lightly held on the extension.

The locking device is designed in such a way that at least one locking element ensures a positive engagement with at least one recess on the extension in a second functional position, so that the syringe closure is held on the extension in a locking manner. The syringe closure is held with the desired final retaining force on the extension and therefore is in the locking position in this second functional position.

Particularly preferred is an example embodiment of the syringe closure characterized in that at least one locking element interacts with the syringe closure in such a way that areas thereof are pushed into at least one recess. These areas of the syringe closure are not so positioned when placed on the extension of a syringe, therefore, that they will contact at least one recess in a positive fit and build retention forces. Rather, it is just possible that these areas are crowded after the first application of the closure on the extension to reach the locking position by at least one locking element into the recess. It is thus possible to attach the syringe closure without exerting great force on the extension of a syringe, and to push areas of the syringe closure into at least one recess only after the attachment under the influence of at least one locking element and thus ensure a secure hold.

In a particularly preferred example embodiment it is provided that the locking device has a number of locking elements, which are allocated to a supporting body with an annular configuration and are arranged thereon at preferably the same peripheral distance to each other. Because several locking elements ensure a positive fit with a recess on the extension in the locking position, a particularly secure hold of the closure on the syringe is ensured. It can be provided at the same time that each locking element has its own allocated separate recess on the extension of the syringe, or that at least a few of the locking elements engage in one common recess. An annular recess, in which all locking elements engage, is particularly preferably provided on the extension.

BRIEF DESCRIPTION OF THE DRAWINGS

Example embodiments will now be described with reference to the drawings.

FIG. 1 shows a longitudinal section of the end of a syringe having a syringe closure directly before the closure is attached on the syringe according to an example embodiment.

FIG. 2 shows the syringe and the syringe closure according to FIG. 1 in the release position directly after attaching the syringe closure on the syringe according to an example embodiment.

FIG. 3 shows the syringe closure firmly attached on the syringe in the locking position according to an example embodiment.

FIG. 4 shows a bottom view of the syringe closure represented in FIGS. 1 to 3 according to an example embodiment.

FIG. 5 shows an oblique perspective top view of a locking device according to an example embodiment.

FIG. 5A shows an oblique perspective top view of another locking device according to another example embodiment.

DETAILED DESCRIPTION

FIG. 1 shows a longitudinal section of a syringe closure 1 according to an example embodiment. The sectional plane is arranged in such a way that the longitudinal axis 3 of the syringe closure 1 is located therein.

The syringe closure 1 is arranged directly above a syringe 5, whose central axis coincides with the longitudinal axis 3. The syringe has a basic body 7, the syringe cylinder, and a terminal extension 9 originating therefrom, which preferentially has a conical configuration and a free end 11. Owing to the conical configuration, the extension 9 tapers from the basic body 7 of the syringe 5 in the direction of its free end 11.

At least one recess 13, which is located herein close to the base 15 of the extension 9 and via which the latter merges into the basic body 7, is provided at a distance from the free end 11 of the extension.

The extension 9 can have one or several such recesses 13, a single annular recess is preferentially provided, in whose area the outer diameter of the basic body 7 is smaller than in an area located above it. The annular recess is located on an imaginary plane, to which the longitudinal axis 3 is perpendicular.

The syringe closure 1 can be designed as a safety and tamper evident seal, as is precisely customary in the medical field. Such syringe closures are preferentially configured in two parts, wherein an upper area 17 is connected to a lower area 19 via a fracture line 21, which is deformed, especially torn open, when the syringe closure 1 is opened, that is, when the upper area 17 is removed, so that manipulations on the syringe closure can be readily detected by a user. Such known syringe closures 1 still have, as a rule, at least one sealing element 23, which seal abuts on the peripheral surface of the extension 9 after the syringe closure 1 is attached and, in particular, likewise its free end 11 is sealed closed.

The syringe closure 1 has a locking device 25, which is provided with at least one locking element 27. In the embodiment shown herein, the locking element 27 engages from below into at least some sections of the syringe closure, that is, from the open side of the syringe closure 1 that faces the syringe 5. An assembled unit is created between the syringe closure 1 and the locking device 25 by means of this preferentially provided arrangement of the locking device 25, so that these two elements can be jointly handled and attached on a syringe 5.

FIG. 1 shows that at least one locking element 27 is arranged in a recess 29, which is delimited radially inwardly by a wall area 31, that is, when observed in direction to the longitudinal axis 3.

FIG. 2 again shows a longitudinal section of the syringe closure 1 and the syringe 5. Same or functionally identical parts are provided with the same reference numerals, so that reference is made in this respect to the description of FIG. 1 in order to avoid repetitions.

FIG. 2 shows that the syringe closure 1 is pushed onto the extension 9 jointly with the locking device 25, wherein the retaining forces that would be necessary to hold the syringe closure 1 on the syringe 5 for transport and mounting are not as yet generated on the extension 9 in this position shown in FIG. 2. The locking device 25 is not activated in the position of the syringe closure 1 shown herein, so that at least one locking element 27 is in a release position.

The locking device 25 is in an unchanged relative position with respect to the syringe closure 1 compared to FIG. 1, wherein a lower rim 33 of the locking device 25 is located at a distance from a shoulder 35 of the basic body 7 of the syringe 5.

FIG. 3 shows the syringe closure 1 on the syringe 5 in a second functional position, namely in the locking position. Here, the syringe closure 1 is pressed completely onto the extension 9, so that the latter is preferentially enclosed all around, but in particular in the area of its free end 11, by the sealing element 23.

The position of at least one recess 13 on the extension 9 is selected in such a way in the embodiment of the syringe closure 1 shown here that the shoulder 35 of the basic body 7 of the syringe 5 displaces the latter into the syringe closure 1 as a result of the abutment on the lower rim 33 of the locking device 25 when the syringe closure 1 is completely pushed onto the syringe 5. In other words: The syringe closure 1 is pushed via the locking device 25, which is fixed in position in the direction of the longitudinal axis 3 after the lower rim 3 hits against the shoulder 35. Thus, there is a relative movement between the syringe closure 1 and the locking device 25, while the syringe closure 1 is pushed into its final position, the locking position, shown in FIG. 3. The syringe closure 1 is securely held on the extension 9 of the syringe 5 in this second functional position.

In the embodiment shown herein, at least one locking element 27 is configured in the shape of a wedge that has a lesser thickness at its upper end 37 than at its lower end 39. At least one locking element 27 thus becomes thicker in the radial direction, that is, perpendicularly to the longitudinal axis 3. The inner surface of at least one locking element 27 is thus configured in an almost conical shape: It tapers from the upper end 37 toward the lower end 39.

As a result of the wedge shape of at least one locking element 27 provided in the embodiment represented herein, the wall area 31 of the syringe closure 1 that interacts with the locking element 27 is pushed in the direction of the longitudinal axis 3 during the displacement of the syringe closure 1 into a locking position so that, owing to the axial displacement of the syringe closure 1 in the direction of the basic body 7 of the syringe 5, a positive engagement with at least one recess 13 is obtained. The latter ensures a secure hold of the syringe closure 1, which assumes the second functional position depicted in FIG. 3 and is in its locking position.

In the embodiment of the syringe 5 shown in FIGS. 1 to 3, at least one recess 13, which is preferentially designed, as already mentioned, as an annular recess, is arranged at such a distance from the shoulder 35 of the basic body 7 of the syringe 5 that the locking device 25 is activated in the position of the syringe closure 1 and the locking device 25 shown in FIG. 3 such that it is in its second functional position, the locking position.

However, if the recess 13—when seen in the direction of the longitudinal axis 3—has a larger distance to the shoulder 35, then the locking device 25 would not be displaced into the syringe closure 1, or at least not as much as shown in FIG. 3, after the syringe 1 is completely attached on the extension 9. It would then have to be ensured by means of a separate tool that the locking device 25 is displaced—in this case upwardly—after the syringe closure 1 is completely attached on the extension 9, so that the wall area 31 is pressed against the outer surface of at least one recess 13 such that a positive engagement is ensured.

The embodiment shown in FIG. 3, in which the shoulder 35 is arranged at such a distance from the lower end 41 of the syringe closure 1 that the locking device 25 is pushed into the syringe closure 1 in such a way that the locking device 25 is fully activated, is, however, particularly preferred: At least one locking element 27 ensures a positive engagement with at least one recess 13 on the extension 9, herein in that the wall area 31 is pressed against the floor of at least one recess 13.

FIG. 4 shows a bottom view of the syringe closure 1. Same and functionally identical parts are provided with the same reference numerals, so that reference is made in this respect to the description of FIGS. 1 to 3.

FIG. 4 shows that the embodiment of the syringe closure 1 shown here does not only have one recess 29, but four recesses 29 preferably arranged at the same peripheral distance with respect to each other when seen in the peripheral direction. The locking device 25 is accordingly configured in such a way that it has four locking elements 27, which are likewise arranged at the same distance from each other—when seen in the peripheral direction—wherein a locking element 27 respectively engages in a recess 29.

FIG. 4 shows that the recesses 29 are inwardly delimited by a wall area 31. It can be provided at the same time that the wall area 31 has a notch 43 in at least one recess 29, in this case, in all recesses, so that the wall area 31 comprises two partial sections 31a, 31b adjacent to the notch 43, which do not touch each other. If the notch 43 is arranged at the very end of a wall area 31, then it results in only one wall section.

If, as explained with reference to FIGS. 1 to 3, the locking device 25 is activated wherein at least one locking element 27, that is, according to FIG. 4 four locking elements, is displaced with reference to the syringe closure 1, the wall area 31, or its wall sections 31a, 31b that are adjacent to the notch 43, are deflected inwardly in the radial direction to the longitudinal axis 23, so that a positive engagement of the wall area 31 or the wall sections 31a, 31b is created with at least one recess 13.

It is possible to allocate a corresponding recess to each of the four wall areas 31 or wall sections 31a, 31b. The syringe closure 1 would then have to be brought in such a rotational position during the attachment on the extension 9 that the wall areas 31 are allocated to corresponding recesses. It is therefore preferentially provided that several wall areas 31 or wall sections 31a, 31b are allocated to a common recess. It is particularly preferred if the recess 13 is configured in annular shape, so that all wall sections 31 engage in this annular recess 13 without requiring a special rotational orientation of the syringe closure 1 with reference to the extension 9.

FIG. 5 shows an oblique perspective top view of an example embodiment of the locking device 25, which has at least one, in this case, preferentially four locking elements 27. The locking elements 27 are connected to each other by means of a supporting element 45 that preferentially supports all of the locking elements 27 of a locking device 25. It is particularly preferably configured in an annular shape. It is also possible at the same time, for example, to also provide annular segments as supporting elements, which are respectively allocated to one or several locking elements. The example embodiment shown here, in which the supporting element 45 is configured in an annular shape and includes all of the locking elements 27, is particularly easy to handle.

It becomes clear that the locking device 25 could also comprise more than four locking elements, in particular, if the syringe closure 1 is correspondingly configured and comprises the preferentially identical number of recesses 29. However, it is also conceivable that one or several of the recesses do not accommodate a locking element, so that there are more recesses than locking elements provided.

In a modified embodiment of the syringe closure 1 it is preferentially provided that at least one recess 29 accommodates a soft, deformable, preferably gel-like material, which functions as a locking element, as shown in FIG. 5A. In this case, the locking device has at least one displacer D, which penetrates into at least one recess 29 and applies pressure on the soft, deformable material during the displacement of the locking device 25, as explained by means of FIGS. 2 and 3. Such displacers D are arranged like the locking elements shown in the figures and—as can be seen in FIGS. 1 to 3—are inserted more and more into a corresponding recess filled with deformable material when a syringe closure 1 is attached. They can be realized without a wedge shape.

In a first example embodiment, the wall area 31 is preferably configured continuous and is deflected radially inwardly in the direction of at least one recess 13 by the soft, deformable material, so that a positive engagement with at least one recess on the extension is obtained.

In another example embodiment, it is preferably provided that at least one recess 29 does not have a closed wall area 31, but two wall sections 31 a, 31 b with a notch 43, through which the soft, deformable material is displaced when the displacer D penetrates into the recess 29 in the direction of at least one recess 13 and creates a positive engagement between the syringe closure 1 and the extension 9. On the one hand, the material of this soft locking element is deformable, such that it is displaced when a displacer D penetrates into the recess 29. On the other hand, it is, also dimensionally stable, such that a secure positive engagement between the syringe closure 1 and the basic body 7 is ensured in the area of at least one recess 13.

In this example embodiment, at least one recess 29 that can be seen in FIGS. 1 to 3 is preferably closed at the top, that is, at a distance from the lower rim 41 of the syringe closure 1, so that the locking element that comprises the soft, deformable material, which can also be made of this material, cannot escape into the interior of the syringe closure, but pushes the wall area 31 into at least one recess 13, or is itself pressed through a notch 43 into this at least one recess in order to ensure the locking position in a second functional position, in which the syringe closure 1 is securely held on the extension 9 by a positive engagement.

The example embodiment of the syringe closure 1 explained with reference to the figures has a locking device 25 with at least one locking element 27, which has an increasing thickness up to its lower end 39 starting at its upper end 37. A wedge shape results in this way. In other words, the locking element 27 is configured as a wedge, which pushes a wall area 31 into a second functional position, the locking position, in at least one recess 13 with an axial relative movement, that is, when seen in the direction of the longitudinal axis 3, in order to ensure a positive fitting.

The following can be especially seen in FIG. 4:

The syringe closure 1 has at least one recess 29, which is inwardly delimited by a wall area 31 that delimits the recess in the direction of the longitudinal axis 3. It is conceivable that this wall area 31—when seen in the peripheral direction—has an increasing thickness, so that the recess 29 tapers from one end to the other end. A wedge shape, which is oriented in the peripheral direction, can thus also be realized. If a locking element, which interacts with the inner side of the wall area 31, is introduced into such a recess with an almost wedge-shaped wall area 31, then a release position can be realized in a first functional position, and a positive engagement with at least one recess 13 on the extension 9 can be realized in a second functional position by means of a relative rotation of the syringe closure 1 with reference to the locking element as a result of the interaction of the locking element with the wedge-shaped wall area 31. In this embodiment, the wall area 31 is pushed inwardly by means of the rotation of the syringe closure 1 with reference to the locking element 27 with a corresponding relative rotation of the wall area 31 with reference to the locking element 27 in order to realize the positive engagement.

In this example embodiment, the locking element itself is not necessarily wedge-shaped. It rather interacts with a wall section 31 acting as wedge—when seen in the peripheral direction—which, in this case, almost represents the locking element of the locking device.

The syringe closure described herein is thus characterized by a locking device with at least one locking element, which ensures a positive engagement with at least one recess on the extension 9 in one functional position, so that the syringe closure 1 is securely held on the syringe 5 in this position, the locking position.

From the explanations concerning the functional principle of the syringe closure 1 it becomes evident that the latter can be attached with extremely low forces on the extension 9 via the free end 11. It has a locking device 25, which is activated after the attachment of the syringe closure 1 and only then ensures the positive engagement with at least one recess 13 on the extension 9 of the syringe 5. In this way, it is possible to prevent an overexpansion of the material as is usual in conventional syringe closures during the attachment of the syringe closure. This leads, on the one hand, to the fact that relatively low forces are required for the attachment of the syringe closure 1 on the extension 9, so that the danger of breaking off the extension 9 is reduced to an absolute minimum. The material of the syringe closure 1 is, on the other hand, protected in such a way that it is not overexpanded and therefore has a longer durability, that is, the material of the syringe closure is only minimally strained even during a relatively long storage time and at great temperature differences during storage or transport of the syringe, so that signs of fatigue and a consequently worse fit of the syringe closure on the syringe is prevented.

In many cases, the syringes are additionally subjected to a final sterilization process after they have been filled and the syringe closure has been attached. It is also provided at the same time that the syringe is autoclaved with the syringe closure. During this process, high temperatures of more than 120° C. occur in particular, at which an overexpanded material of the syringe closure is changed in such a way that the retaining forces of the syringe closure on the syringe highly decrease. This can lead to an unintentional detachment of the syringe closure 1.

It was explained with reference to FIG. 1 that the locking device 25 has at least one locking element 27, which is inserted into a recess 29 of the syringe closure 1 in some sections, so that a preassembled unit according to FIGS. 1 and 2 results, in which the syringe closure 1 and the locking device 25 can be jointly handled. It is preferentially provided at the same time that the locking device 25 is locked in the syringe closure 1, that is, it is connected to the syringe closure 1 via a snap connection.

It is also conceivable, however, that the syringe closure 1 and the locking device 25 are configured in one piece, that consequently the locking device 25 is part of the syringe closure and is connected thereto, for example, by means of at least one web or thin-walled material area. If a force is applied to the locking device 25, the webs or connection area tear, that is, an axial displacement of the locking device 25 in the direction of the longitudinal axis 3 can occur, as explained with reference to FIGS. 1 to 3.

It is finally possible to produce the syringe closure 1 and the locking device 25 in a two-component injection molding process, wherein the syringe closure 1 and the locking device 25 are comprised of plastic components, which are not connected to each other during the production process in such a way that a relative movement of the two elements with respect to each other would be prevented.

In summary, a syringe closure for a syringe 5 is provided having a basic body 7, a terminal extension 9 that extends from the basic body 7, which has a free end 11 and a base 15 arranged on the basic body 7. At least one recess 13 is provided on the extension 9 at a distance from its free end 11. The syringe closure 1 for closing off the syringe 5 can be attached in such a way on its extension 9 via its free end 11 that the syringe closure 1 overlaps at least one recess 13 of the extension 9, and is characterized by a locking device 25 having at least one locking element 27, which assumes a release position in a first functional position after the attachment of the syringe closure 1 on the extension 9, and ensures a positive engagement with at least one recess 13 on the extension 9 in a second functional position, the locking position, and thus lockingly holds the syringe closure 1 on the extension 9.

According to an example embodiment, the locking device 25 has at least one wedge. The wedge interacts with at least one locking element 27 and displaces said locking element into the locking position. At least one locking element 27 interacts with the syringe closure 1 and presses areas of the syringe closure 1 into at least one recess 13 to realize the locking position.

According to another example embodiment, at least one locking element 27 is itself configured as a wedge and interacts with areas of the syringe closure 1.

According to an example embodiment, the locking device 25 has a number of locking elements 27, which are allocated to one supporting element 45.

According to a further example embodiment, the supporting element 45 is configured in an annular shape and the locking elements 27 are preferentially arranged at an identical peripheral distance to each other, wherein a recess is allocated to each of the locking elements 27, or at least some of the locking elements 27 engage into a joint recess.

According to yet another example embodiment, the syringe closure 1 has at least one recess 29, in which the locking element 27 can be arranged. The recess 29 has at least one deformable wall area 31. The wall area 31 has a notch 43. At least one locking element has a deformable material or is made therefrom, the locking device has a displacer, which applies pressure to the deformable material of the locking element in the locking position, so that at least one deformable wall area 31 can be pushed into at least one recess 13, or the deformable material can be pressed into at least one recess 13.

What is claimed is:

1. An apparatus for closing a syringe, the syringe having a basic body with a terminal extension that extends from the basic body, the terminal extension having a free end, a base, and at least one first recess which is provided on the terminal extension at a distance from the free end, the apparatus being attached to the syringe for closing off the syringe on the terminal extension of the basic body of the syringe via its free end in such a way that the apparatus overlaps the at least one first recess of the terminal extension, the apparatus comprising:
   a syringe closure including:
      an open side facing the syringe; and
      a second recess that is delimited radially inwardly by an inner wall area and radially outwardly by an outer wall area of the syringe closure, wherein the inner wall area forms at least one deformable wall; and
   a locking device having at least one locking element which assumes a release position when the locking device is in a first functional position relative to the syringe closure after an attachment of the syringe closure on the terminal extension, and which assumes a locking position after the locking device is moved from the first functional position to a second functional position relative to the syringe closure, wherein the locking element in the locking position ensures a positive engagement with the at least one first recess on the terminal extension and engages into the second recess of the syringe closure from the open side when the locking device is in the second functional position, and thus lockingly holds the syringe closure on the terminal extension, and wherein the at least one locking element interacts with the at least one deformable wall of the syringe closure and presses the inner wall area into the at least one first recess to realize the locking position.

2. The apparatus according to claim 1, wherein the at least one locking element comprises a wedge.

3. The apparatus according to claim 2, wherein the wedge interacts with a wall area of the at least one deformable wall of the syringe closure and displaces the wall area of the at least one deformable wall into the locking position.

4. The apparatus according to claim 1, wherein the at least one locking element is configured as a wedge and interacts with areas of the at least one deformable wall of the syringe closure.

5. The apparatus according to claim 1, wherein the locking device comprises a plurality of locking elements which are allocated to one supporting element.

6. The apparatus according to claim 5, wherein the supporting element is configured in an annular shape and the locking elements are arranged at an identical peripheral distance to each other.

7. The apparatus according to claim 5, wherein a plurality of first recesses are provided on the terminal extension of the syringe, and wherein each of the plurality of locking elements is allocated to a respective one of the plurality of first recesses.

8. The apparatus according to claim 5, wherein at least some of the plurality of locking elements are configured to engage into a joint first recess on the terminal extension of the syringe.

9. The apparatus according to claim 1, wherein the at least one deformable wall area has a notch.

10. The apparatus according to claim 1, wherein the second recess accommodates a deformable material,
   wherein the at least one locking element of the locking device is configured as a displacer, which applies pressure to the deformable material in the locking position, so that the at least one deformable wall area can be pushed into the at least one first recess, or the deformable material can be pressed into the at least one first recess.

11. The apparatus according to claim 1, wherein the syringe closure is movable in an axial direction relative to the locking device between the first functional position and the second functional position.

* * * * *